US011622743B2

(12) United States Patent
Huang et al.

(10) Patent No.: US 11,622,743 B2
(45) Date of Patent: *Apr. 11, 2023

(54) RIB BLOCKAGE DELINEATION IN ANATOMICALLY INTELLIGENT ECHOCARDIOGRAPHY

(71) Applicant: KONINKLIJKE PHILIPS N.V., Eindhoven (NL)

(72) Inventors: Sheng-Wen Huang, Ossining, NY (US); Emil George Radulescu, Ossining, NY (US); Ramon Quido Erkamp, Yorktown Heights, NY (US); Shougang Wang, Ossining, NY (US); Karl Erhard Thiele, Andover, MA (US); David Prater, Andover, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 404 days.

This patent is subject to a terminal disclaimer.

(21) Appl. No.: 16/836,985

(22) Filed: Apr. 1, 2020

(65) Prior Publication Data

US 2020/0237337 A1 Jul. 30, 2020

Related U.S. Application Data

(63) Continuation of application No. 14/901,114, filed as application No. PCT/IB2014/062359 on Jun. 18, 2014, now Pat. No. 10,631,821.

(Continued)

(51) Int. Cl.
*A61B 8/08* (2006.01)
*G01S 7/52* (2006.01)
(Continued)

(52) U.S. Cl.
CPC ............ *A61B 8/0841* (2013.01); *A61B 5/339* (2021.01); *A61B 6/5205* (2013.01); *A61B 8/085* (2013.01);
(Continued)

(58) Field of Classification Search
CPC ..... A61B 8/0841; A61B 5/339; A61B 6/5205; A61B 8/085; A61B 8/0883; A61B 8/463;
(Continued)

(56) References Cited

U.S. PATENT DOCUMENTS 7,933,007 B2 4/2011 Stanton
10,631,821 B2 * 4/2020 Huang ................. A61B 8/5269
2009/0141957 A1 6/2009 Yen

FOREIGN PATENT DOCUMENTS

WO 2014097090 A1 6/2014

OTHER PUBLICATIONS

Lovstakken, Lasse et al "Real Time Indication of Acoustic Window for Phased-Array Transducers in Ultrasound Imaging", 2007 IEEE Ultrasonics Symposium.

(Continued)

*Primary Examiner* — Jonathan Cwern (57) ABSTRACT

A method for using an interactive visual guidance tool for an imaging acquisition and display configured for user navigation with respect to a blockage of a field of view detects, and spatially defines, the blockage. It also integrates, with the image for joint visualization, an indicium that visually represents the definition. The indicium is moved dynamically according to movement, relative to the blockage, of the field of view. The indicium can be shaped like a line segment, or two indicia can be joined in a "V" shape to frame a region of non-blockage. The defining may be based on determining whether ultrasound beams in respective directions are blocked.

9 Claims, 8 Drawing Sheets

Related U.S. Application Data (60) Provisional application No. 61/840,696, filed on Jun. 28, 2013.

(51) Int. Cl.
*A61B 6/00* (2006.01)
*A61B 8/00* (2006.01)
*G01S 15/89* (2006.01)
*A61B 5/339* (2021.01)

(52) U.S. Cl.
CPC ............ *A61B 8/0883* (2013.01); *A61B 8/463* (2013.01); *A61B 8/5269* (2013.01); *A61B 8/54* (2013.01); *G01S 7/52047* (2013.01); *G01S 7/52085* (2013.01); *G01S 15/8927* (2013.01); *G01S 15/8977* (2013.01); *A61B 8/4488* (2013.01); *A61B 8/461* (2013.01); *A61B 8/483* (2013.01)

(58) Field of Classification Search
CPC ....... A61B 8/5269; A61B 8/54; A61B 8/4488; A61B 8/461; A61B 8/483; G01S 7/52047; G01S 7/52085; G01S 15/8927; G01S 15/8977

See application file for complete search history.

(56) References Cited

OTHER PUBLICATIONS

Seo, Chi Hyung et al "Sidelobe Suppression in Ultrasound Imaging using Dual Apodization with Cross-Correlation", IEEE Transaction on Ultrasonics, Ferroelectrics, and Frequency Control, vol. 55, No. 10, Oct. 2008.

Mallart, Raoul et al "Adaptive Focusing in Scattering Media Through Sound-SPeed Inhomogeneities: The van Cittert Zemike Approach and Focusing Criterion", Journal Acoustical Society of America, vol. 96, No. 6, Dec. 1994.

Hollman, K.W. et al "Coherence Factor of Speckle from a Multi-Row Probe", 1999 IEEE Ultrasonics Symposium.

\* cited by examiner

$$\rho(r,\theta) \equiv \frac{C[b_1(r,\theta), b_2(r,\theta)]}{\sqrt{C[b_1(r,\theta), b_1(r,\theta)]} \sqrt{C[b_2(r,\theta), b_2(r,\theta)]}}$$

where $$C[b_k(r,\theta), b_\ell(r,\theta)] \equiv \int_{-\infty}^{\infty} \int_{-\infty}^{\infty} w[r'(r,\theta) b_k(r+r', \theta+\theta') b_\ell(r+r', \theta+\theta') dr' d\theta';$$

and where $$b_k(r,\theta) = \sum_{j \in C_k} s_j(r,\theta)$$

RIB BLOCKAGE DELINEATION IN ANATOMICALLY INTELLIGENT ECHOCARDIOGRAPHY

FIELD OF THE INVENTION

The present invention relates to tracking a spatial limit of visual blockage and, more particularly, to an interactive visual guidance tool for such tracking.

BACKGROUND OF THE INVENTION

Successful ultrasound scanning relies strongly on the training and experience of the user. Echocardiography scans are especially challenging as the heart is surrounded by ribs and lung tissue. Ultrasound can barely penetrate calcified ribs (typically encountered in the apical view) and lung tissue because of severe acoustic impedance mismatch between them and surrounding body tissue. In addition, ultrasound absorption in ribs is quite high compared to that of soft tissue. To avoid artifacts, the user has to place the probe in the right position, i.e., to find a good acoustic window, for imaging. Conventionally, this is done solely based on real-time ultrasound images displayed onscreen. Although experienced users are usually capable of recognizing image degradation, and of improving image quality accordingly by moving the probe to a better position, less experienced users might acquire compromised images because of inferior hand-eye coordination and less awareness of artifacts.

SUMMARY OF THE INVENTION

What is proposed herein below is directed to addressing one or more of the above concerns.

There exists a need for a tool that can guide, in real time, and train inexperienced or less experienced users to position the probe for optimal image quality.

To guide and train inexperienced or less experienced users to place the probe in the right position, it is proposed herein to help users with hand-eye coordination by providing a reversed "V" display superimposed on the images. Each of the two legs of the "V" indicates an edge of blockage such as by a rib, one leg per rib for instance. Each of the two legs of the "V" moves in real time according to movement of the field of view of the probe relative to the blockage. The field of view may move according to movement of the probe for example. The leg movement may be seen onscreen as respective real-time rotations of the legs so that they, while maintaining their "V" shape, continue to frame whatever is the current region of non-blockage in the ultrasound image currently onscreen. The field of view may be three-dimensional, in the case of a matrix probe. Or the field of view may be within an imaging plane, in the case of matrix probes or one-dimensional, i.e., 1D, probes. The imaging plane may be rotated either electronically or by manual manipulative control, while the interactive feedback appears onscreen. In particular, the rotation can be such as to rotate the imaging plane into and out of alignment with respective x-planes, the indicia moving dynamically according to the rotating. More than one ultrasound view, and respectively more than one indicium, e.g., "V" leg, or indicium pair may be viewable onscreen, concurrently for example. In particular, presented for viewing may be one image in one imaging plane and simultaneously another image in another, different imaging plane or x-plane, the indicia in both images moving dynamically with a change in field of view relative to the blockage.

The indicium may alternatively be a coloring added to the screen in place of or complementing the V-leg graphic overlay, so that the coloring appears, for example, throughout the region of blockage seen onscreen.

In accordance with an aspect of the present invention, an interactive visual guidance tool is for a device that includes a display; an imaging probe; and a view rendering module configured for presenting, on the display, an image acquired via the probe. The tool is configured for user navigation with respect to a blockage of a field of view. The tool includes: a blockage module configured for detecting, and spatially defining, the blockage; and a demarcation tracking processor configured for integrating, with the image for joint visualization on the display, an indicium that visually represents the definition. The tool is configured for moving the indicium dynamically according to movement of the field of view relative to the blockage.

As a sub-aspect, the image includes an ultrasound image.

In a further sub-aspect, the tool includes, for deriving the image, imaging channels for receiving image data via the probe. For the data received on the channels and with focusing delays having been applied, a metric of similarity among the data is computed. The defining is based on the metric.

In a still, further sub-aspect, the metric is representative of a correlation between beamsummed data of different apertures, the channels being divided among the apertures.

As a yet further sub-aspect, the apertures are interleaving complementary apertures.

In a particular, still further sub-aspect, the channels are randomly divided among the apertures.

In another sub-aspect, whether ultrasound beams in respective directions are blocked is determined, the defining being based on a result of the determining.

In a sub-aspect of this, the tool has, for deriving the image, imaging channels for receiving image data via the probe. A metric of coherence of the data received on the plural channels is computed. The determination of blockage/non-blockage for a direction is based on the metric for locations in that direction.

In one further sub-aspect of this, determination, in a direction, is based on whether the metric indicates a predetermined level of coherence for at least a predetermined number of locations, in that direction, for which the metric was computed.

In a different sub-aspect, the field of view is V-shaped with the point of the V at said probe.

As a related sub-aspect the indicium is shaped like a line segment.

In one sub-aspect of this, there is integrating, with the image for joint visualization on the display, a second indicium that visually represents the definition. The tool is further configured for moving the second indicium dynamically according to movement of the field of view relative to the blockage. The indicia jointly are V-shaped.

In another sub-aspect, the indicium represents a spatial border of the blockage.

As an alternative sub-aspect, the integrating involves adding, to the image, color as the indicium.

As an additional sub-aspect, the image is shaped like a sector of a circle.

In yet another sub-aspect, the probe is a matrix probe, with the field of view being three-dimensional. With respect to the same probe position, another indicium is integrated with another image for joint visualization on the display, the two images being in different imaging planes. The tool is further configured for moving said another indicium dynamically according to movement of the field of view relative to blockage in the respective, different imaging plane.

As a sub-aspect of the above, said another image and said image are displayed concurrently on the display.

In a specific sub-aspect, the detecting, and the defining, are with respect to, as a cause of said blockage, a rib of a human or of an animal.

In a particular sub-aspect, a fraction of sampled locations within the field of view that have valid data is calculated. An indicator of the calculated fraction is shown on the display.

In one version of the tool, the field of view is within an imaging plane. The blockage is with respect to imaging in the imaging plane.

In a further sub-version, the tool is configured for rotating the imaging plane into and out of alignment with respective x-planes and for moving the indicium dynamically according to the rotating.

In a still further sub-version, the imaging plane is transverse to one or more ribs causing the blockage.

In one more sub-aspect, the field of view is a field of view of the probe.

Details of the novel, real-time, interactive visual guidance technology are set forth further below, with the aid of the following drawings, which are not drawn to scale.

DETAILED DESCRIPTION OF EMBODIMENTS

Figure 1:
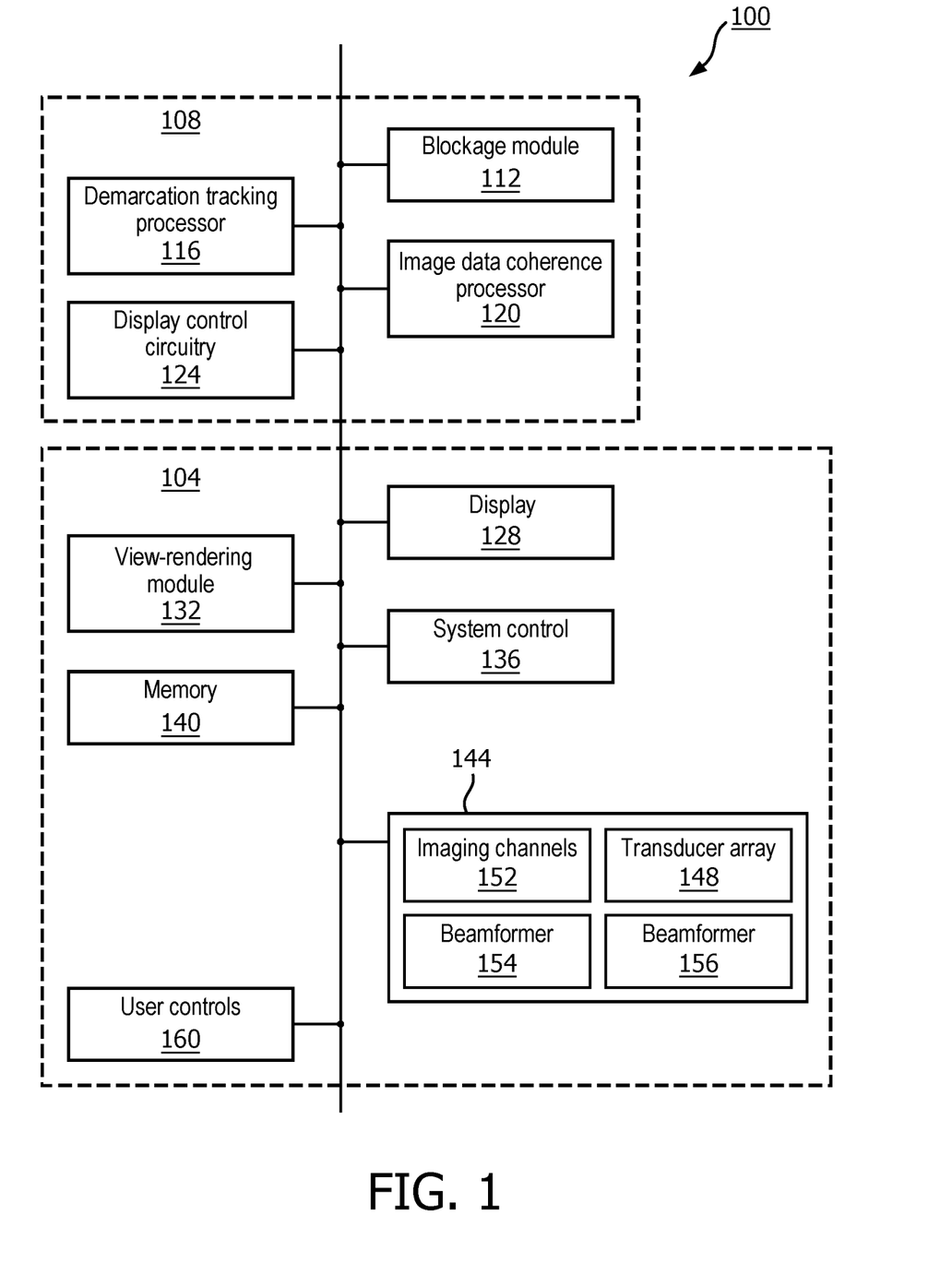
FIG. 1 is a schematic diagram of an ultrasound technician interactive guidance apparatus in accordance with the present invention.

FIG. 1 depicts, by way of illustrative and non-limitative example, an ultrasound technician interactive guidance apparatus 100. The apparatus 100 includes a medical ultrasound device 104 and an interactive visual guidance tool 108. Included in the tool 108 are a blockage module 112, a demarcation tracking processor 116, an imaging data coherence processor 120 and display control circuitry 124. The medical ultrasound device 104 includes a display 128; a view rendering module 132; a system controller 136; memory 140; an imaging probe 144 having a transducer array 148, imaging channels 152 and beamformers 154, 156; and user controls 160. The blockage module 112 detects, and spatially defines, the blockage. The demarcation tracking processor 116 integrates, with an ultrasound image for joint visualization on the display 128, an indicium that visually represents the spatial definition by the blockage module 112. The imaging data coherence processor 120 correlates imaging data acquired via complementary apertures of the probe 144.

Figure 2:
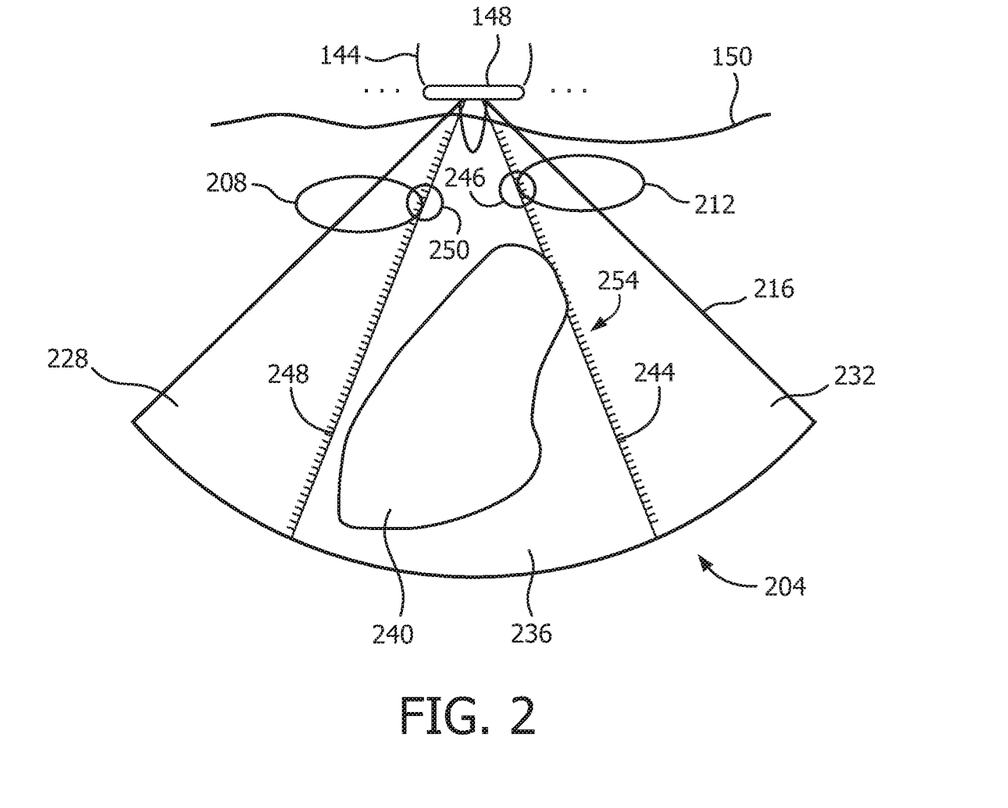
FIG. 2 is an illustration showing an example of imaging-blockage demarcation, and the directions of blockage, in accordance with the present invention.

FIG. 2 shows a representation of a fan-shaped ultrasound image 204 or sonogram acquired via the transducer array 148 with the imaging probe 144 placed intercostally and against the skin 150 of a human being or animal. The imaging plane is transverse to the ribs 208, 212 which partially block a field of view 216 of the probe 144. As discussed herein above, from the image 204 alone, without added graphics, the blockage may not be easily discernable to an inexperienced clinician. The ribs 208, 212 and/or lungs (not shown) cause blockage of the imaging. The blockage is characterizable by regions 228, 232 of blockage on both sides of a region 236 of non-blockage. Imaging of a heart 240 is partially blocked by the rib 212 shown on the right side. An onscreen indicium 244 visually represents the spatially defined blockage, is shaped like a line segment extending to a curved portion of the fan-shaped, or sector-shaped, image 204, and is superimposed on the image for joint visualization. The field of view 216 may change, by probe movement for instance. During the change, the indicium 244 moves circumferentially on-screen in real time to remain indicative of imaging blockage, e.g., by the rib 212 shown on the right, of the current onscreen image 204. In particular, the demarcation tracking processor 116 estimates an angle of a left edge 246, of the rib 212 shown on the right, relative to the imaging aperture of the transducer array 148. A second indicium 248 also tracks blockage in real-time based on a right edge 250 of the rib 208 shown in FIG. 2 on the left side, the indicia jointly remaining "V" shaped with the point of the "V" at the probe 144. Hash marks 254 running along the outside of the two legs of the "V" indicate the region of blockage. The ribs 208, 212 shown in FIG. 2 would not appear onscreen; instead, their presence is tracked by means of the indicia 244, 248. The heart 240 shown in FIG. 2 could appear onscreen as a graphic generated to represent a segmentation based on the ultrasound imaging. Or the heart 240 may appear onscreen as merely part of the ultrasound image 204. Although the focus of discussion herein relates to rib-based blockage, blockage can also be due to lung tissue, and the tracking indicia 244, 248 will automatically frame regions 228, 232 of blockage.

Coherence of channel data is used to detect blockage. Each channel delivers its respective radiofrequency data magnitude associated with its respective fixed transducer element or patch of elements. As ultrasound echoes return, their incident pressures on the elements are sampled quickly and periodically. The samples are delayed with respect to each other according to the line-of-sight travel time geometry of the field point being evaluated. Here, "coherence" means similarity among data recorded by different channels of an array after applying the above-mentioned receiving focusing delays.

One gauge of coherence is a beamsummed-data-based coherence estimation method, such as the one described in U.S. Patent Publication No. 2009/0141957 to Yen et al., the entire disclosure of which is incorporated herein by reference.

Figure 3:
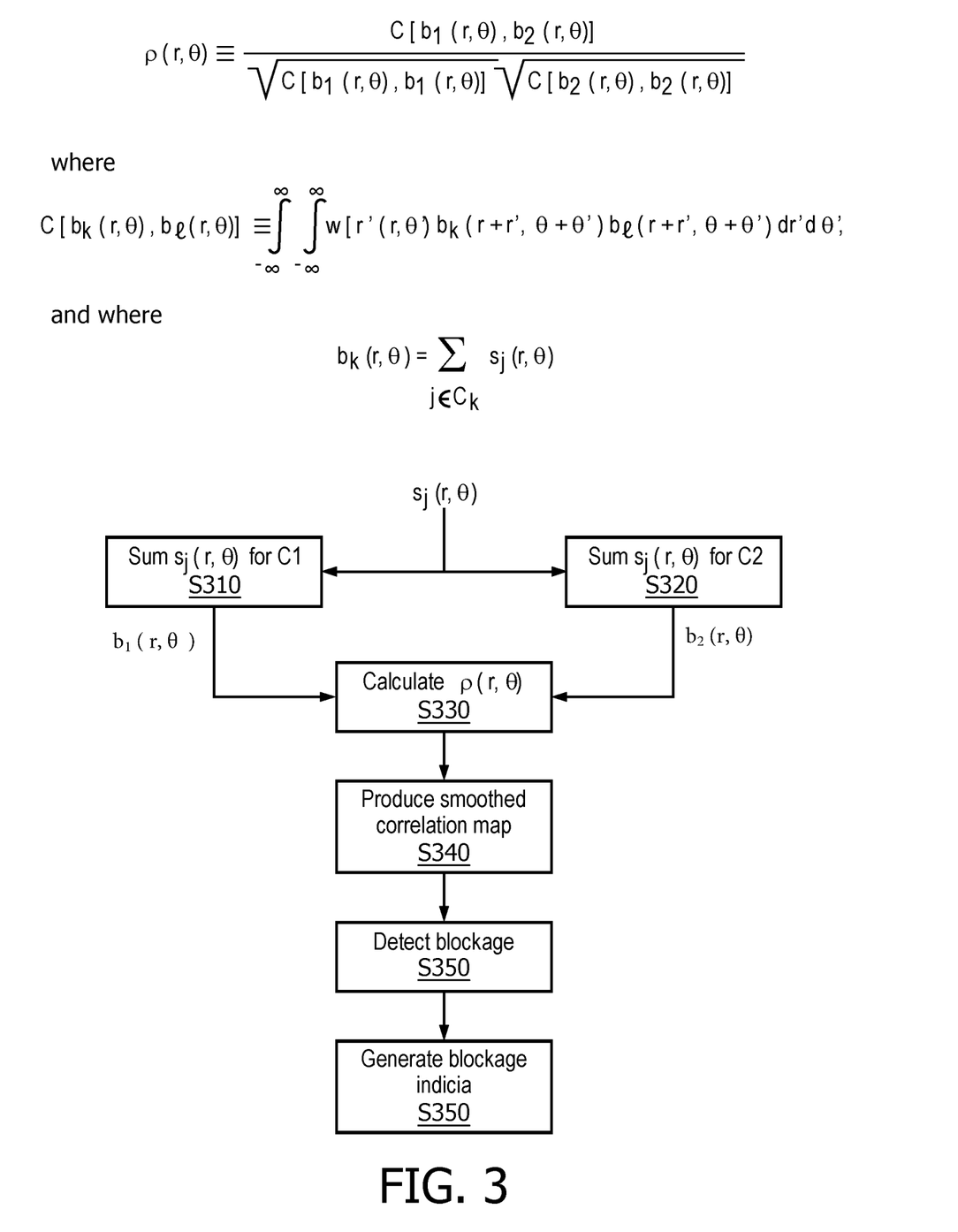
FIG. 3 is flow chart, and formula list, relating to coherence-based spatial discrimination and view blockage boundary determination based on the discrimination, in accordance with the present invention.

The estimation method can be tailored to detecting rib and lung blockage, and is demonstrated below using the two beamformers 154, 156. Let $s_j(r, \theta)$ denote the (real-valued) channel data at depth r along the receive beam in the direction $\theta$, that data received by the j-th channel after applying the focusing delay, and let $C_1$ and $C_2$ denote the set of channels used in the first and the second beamformer 154, 156, respectively. The output of the k-th (k=1, 2) beamformer is $b_k(r, \theta)$, the formula for which is shown in FIG. 3. When all the channel data $s_j(r, \theta)$ are identical across channels, $b_1(r, \theta)$ and $b_2(r, \theta)$ will be highly correlated no matter how $C_1$ and $C_2$ are chosen. On the other hand, when the channel data are mainly contributed by scatterers in sidelobe regions, the correlation between $b_1$ and $b_2$ can drop significantly if $C_1$ and $C_2$ are properly chosen. $C_1$ and $C_2$ can be complementary, interleaving apertures. In short, it is possible to distinguish between on-axis signals and off-axis signals based on correlation between $b_1$ and $b_2$. The output of the correlator is the correlation coefficient $\rho(r, \theta)$ of $b_1(r, \theta)$ and $b_2(r, \theta)$ defined as listed in FIG. 3, where w is a real symmetric weighting function. $\rho(r, \theta)$ is then lowpass filtered to get a smoothed correlation map $\hat{\rho}(r, \theta)$ which is used for blockage detection. The correlation coefficient $\rho(r, \theta)$ serves a metric of similarity, or metric of coherence, among the data received on the imaging channels with focusing delays having been applied. It is representative of a correlation between beamsummed data of different apertures, with the imaging channels being divided among the apertures. The division may be random, as discussed further below.

A flow diagram for the algorithm is shown in FIG. 3. Sums of $s_j(r, \theta)$ are taken for $C_1$ (step S310) and for $C_2$ (step S320). They are correlated to calculate the correlation coefficient $\rho(r, \theta)$ (step S330) which is low-pass filtered (step S340) to produce the smoothed correlation coefficient map, or "correlation map" $\hat{\rho}(r, \theta)$ used for blockage detection (step S350). The indicia 244, 248, each serving as a spatial border between blockage and non-blockage, are then generated for presentation in the inverted "V" display (step 360).

In a specific example, the data is acquired at 32 MHz sampling rate in a pulse-inversion mode using a probe having 80 transducer elements. Each frame has 44 beams and the beam density is 0.4944 beam/degree. The center frequency is 1.3 and 2.6 MHz on transmit and on receive, respectively. $C_1$={20-22, 26-28, 32-34, 38-40, 44-46, 50-52, 56-58} and $C_2$={23-25, 29-31, 35-37, 41-43, 47-49, 53-55, 59-61}. The weighting function w used in the correlator is a 51 (axially or in the r direction) by 1 (laterally or in the $\theta$ direction) boxcar and the smoothing filter is a 501 by 3 boxcar.

Due to the periodic structure of the apertures, sensitivity of the correlation coefficient $\rho$ to off-axis signals varies periodically with the direction of off-axis signals.

This periodicity can be alleviated by randomizing sub-aperture sizes while still keeping both apertures complementary. In other words, the channels are randomly divided among the apertures.

An example of random complementary apertures is $C_1$={21-22, 26-28, 30-31, 35, 37, 39, 41-45, 49, 51, 53, 57, 60-61} and $C_2$={20, 23-25, 29, 32-34, 36, 38, 40, 46-48, 50, 52, 54-56, 58-59}.

To verify whether a beam, and thus its direction, is blocked, a count is made of the number of points with a correlation coefficient ($\hat{\rho}$) higher than 0.55 between 72 and 180 mm in depth. If at least 400 points (at 32 MHz sampling rate) in a beam have high coherence, this beam is considered penetrating into tissue. Otherwise it is considered blocked by a rib.

The upper bound of the depth range is not critical. 72 mm, much larger than the depth of human ribs in general, can be chosen as the lower bound because high coherence or correlation coefficient values might be present in regions right below a rib due to multiple reflections (or reverberation) and such reflections tend to fade away with depth.

The apertures described do not include channels in both ends of the full aperture. Though apertures can be extended to include those channels, the number of blocked beams might be underestimated if large apertures are used. This is because the correlation coefficient of complementary aperture outputs could still be high if part of the large complementary apertures is not blocked.

Figure 4:
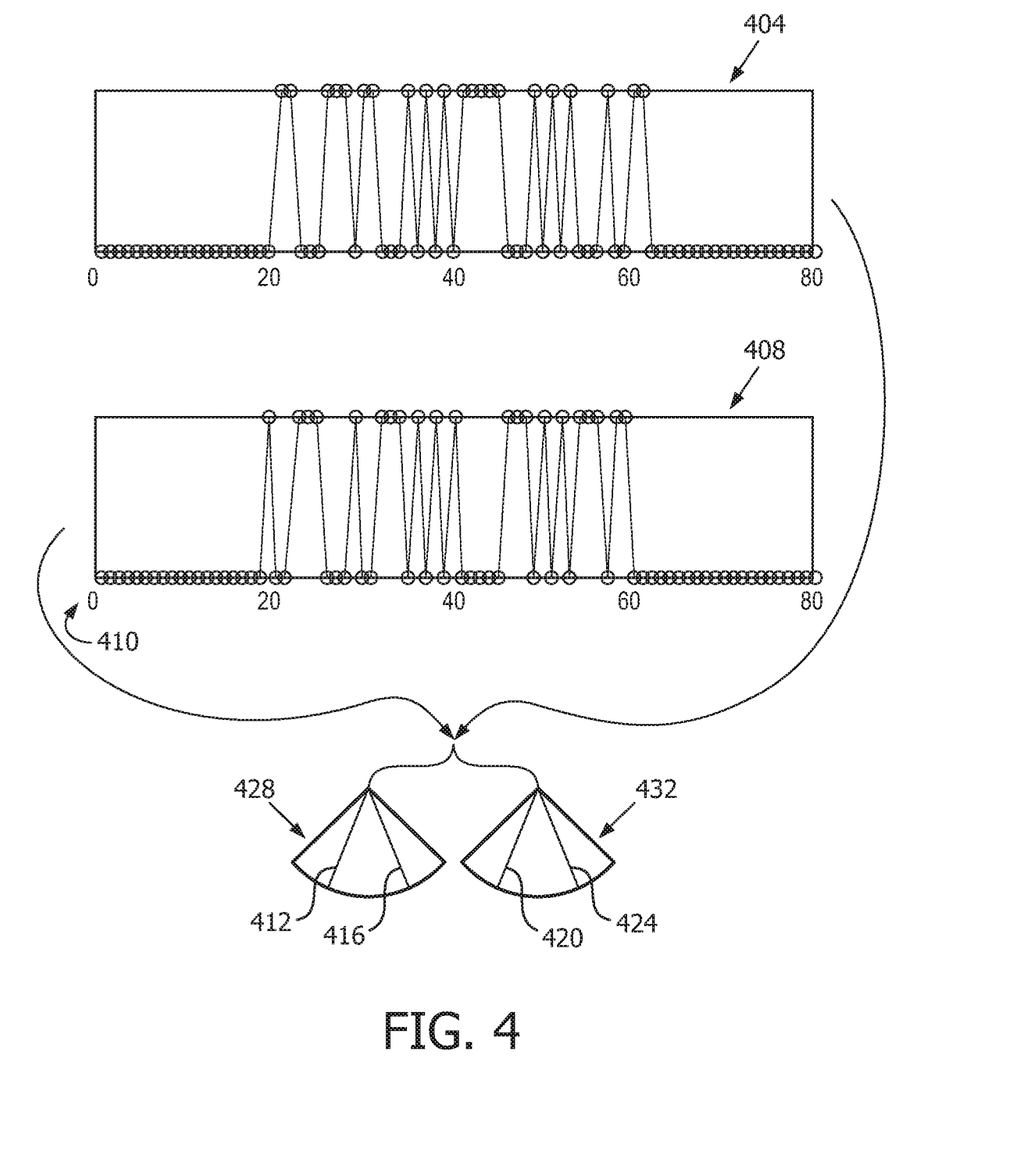
FIG. 4 is a conceptual diagram illustrating random complementary transducer array apertures, and their use in tracking spatial limits of visual blockage.

FIG. 4 illustrates random complementary transducer array apertures, and their use in tracking spatial limits of visual blockage. An aperture 404 ($C_1$) is set for the first beamformer 154 and an aperture 408 ($C_2$) is set for the second beamformer 156. Imaging channels 410 are represented along the horizontal axis. Beamsummed output of the apertures 404, 408 is correlated to discern indicia 412, 416, 420, 424 superimposed on two side-by-side displayed sonograms 428, 432 representative of different imaging planes.

Figure 5:
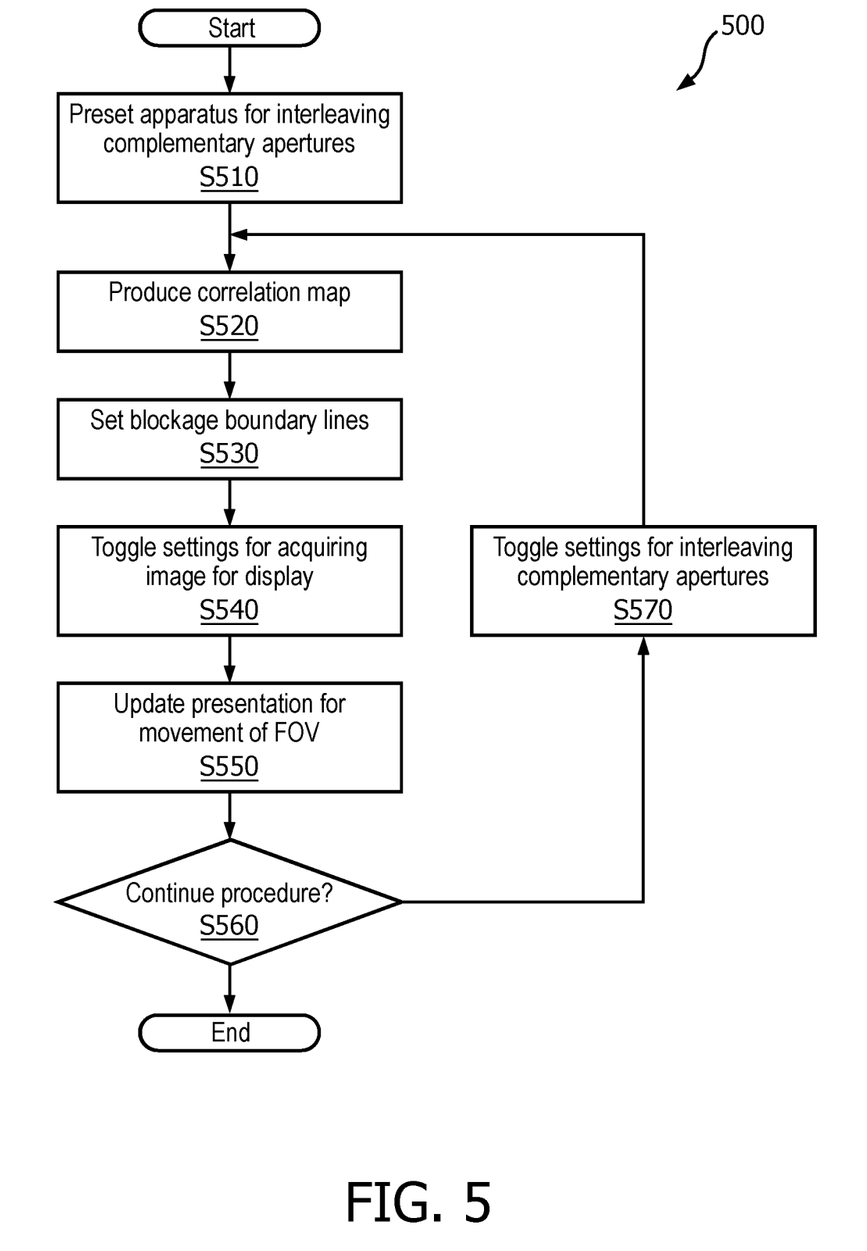
FIG. 5 is a flow chart of overall operation of one implementation of the apparatus of FIG. 1, in accordance with the present invention.

FIG. 5 demonstrates an exemplary procedure 500 for overall operation of one implementation of the apparatus 100. The apparatus 100 is pre-set, during initialization, for interleaving complementary apertures, such as random interleaving complementary apertures (step S510). The correlation map of step S350 is produced (step S520). Based on the correlation map $\hat{\rho}(r, \theta)$, blockage boundary lines are set (step S530). The aperture settings are toggled back for acquiring an ultrasound image for display (step S540). The presentation is updated, as by refreshing the display, for movement of the field of view 216 (step S550). If the procedure 500 is to continue (step S560), the aperture setting are toggled back to yield (random) interleaving complementary apertures (step S570), and processing branches back to derivation of the correlation map in step S520.

Figure 6A:
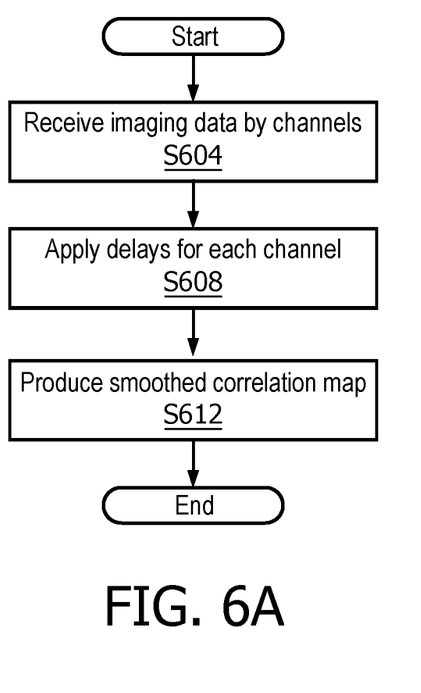
FIG. 6A is a flow chart of an example of coherence map derivation, in accordance with the present invention.

FIG. 6A is a more detailed description of the correlation map formation in step S520. Imaging data is received by the channels 410 of the complementary apertures 404, 408 (step S604). Focusing delays are applied by channel. Each of the beamformers 154, 156 does this separately (step S608). The delayed data is beamsummed by the respective beamformers 154, 156; the beamsummed data of one of the beamformers 154, 156 is correlated with that of the other to calculate the correlation coefficient $\rho(r, \theta)$; the correlation coefficients $\rho(r, \theta)$ are ordered by imaging depth in the axial direction and laterally in the beam direction; and the coefficients are low-pass filtered and smoothed, to complete the map $\hat{\rho}(r, \theta)$, as in steps S310-S350 (step S612).

Figure 6B:
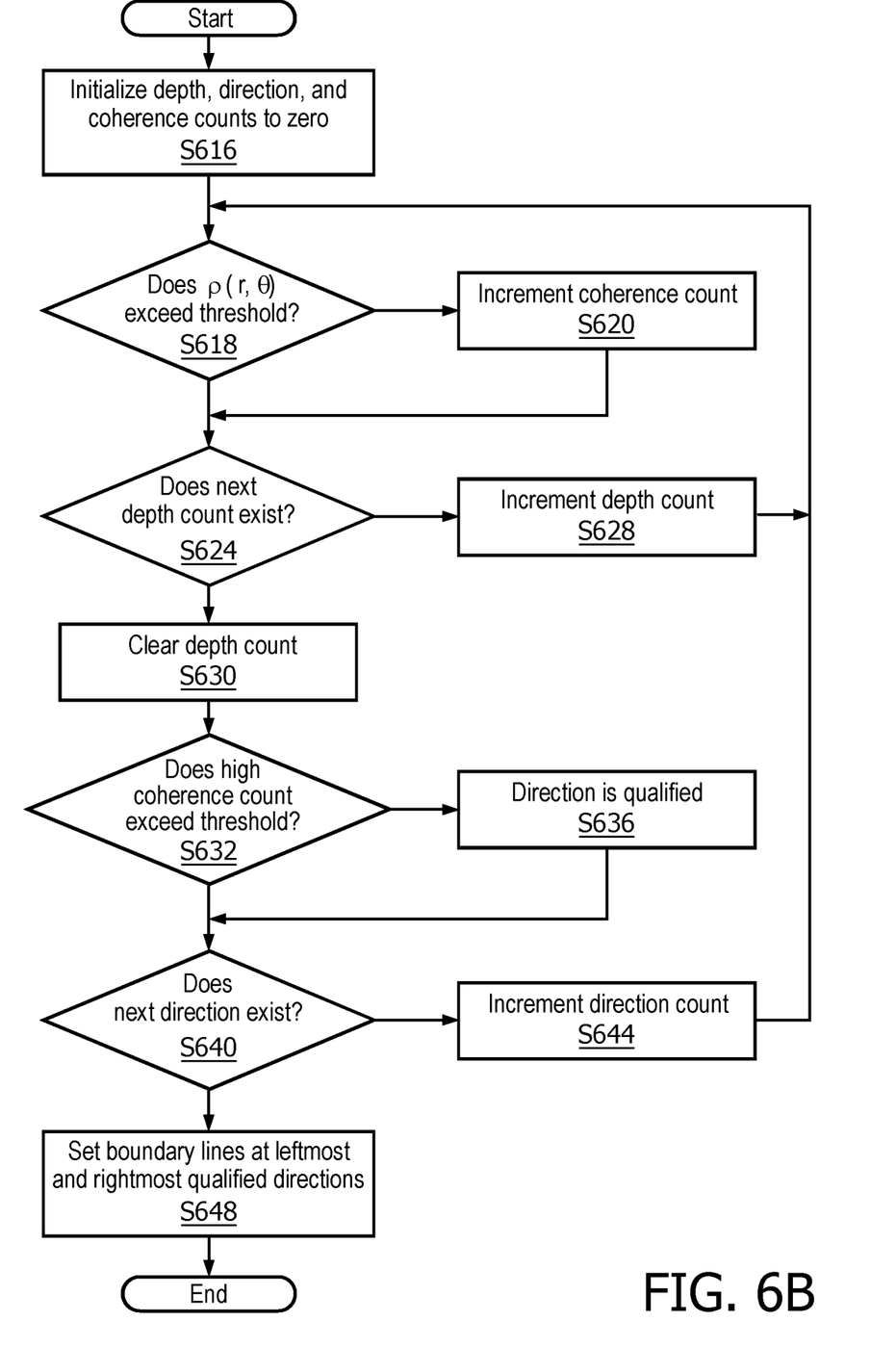
FIG. 6B is a flow chart of an example of boundary line determination, in accordance with the present invention.

FIG. 6B is a more detailed description of boundary line determination of step S530. A current direction and a current imaging depth are respectively initialized to the first direction and the first depth. The depth, direction, and coherence counts are initialized to zero (step S616). If the current correlation coefficient $\rho(r, \theta)$ in the completed map exceeds the predetermined correlation threshold (S618), a predetermined level of coherence is deemed to exist for that location (r, $\theta$) and the coherence count is incremented (step S620). In either event, if a next imaging depth exists (step S624), the depth count is incremented (step S628) and return is made to step S618. If, on the other hand, a next imaging depth does not exist (step S624), the depth count is cleared (step S630), and query is made as to whether the coherence count exceeds a predetermined qualification threshold, i.e., whether a sufficient number of correlation coefficients $\rho(r, \theta)$ for respective imaging depths along the current direction each indicate sufficiently high correlation (step S632). If the qualification threshold is exceeded (step S632), the direction is deemed to be qualified (step S636). In either case, if a next direction exists (step S640), the direction count is incremented (step S644), and return is made to step S618. Otherwise, if there is no next direction (step S640), the boundary lines are set at the leftmost and rightmost qualified directions to spatially define the blockage (step S648). The boundary lines in FIG. 2 are the indicia 244, 248.

As an alternative to line-by-line processing of the correlation map $\hat{\rho}(r, \theta)$, an image can be derived from the map by image or morphological processing such as dilation/erosion that rejects outliers and/or suppresses error. After processing, the indicia 244, 248 are the lines that frame the output region. They will inherently indicate onscreen, to the user, beam directions that lie outside the indicia, i.e., in which beams are blocked as presently evidenced by lack of imaging data coherence along the beam.

Figure 6C:
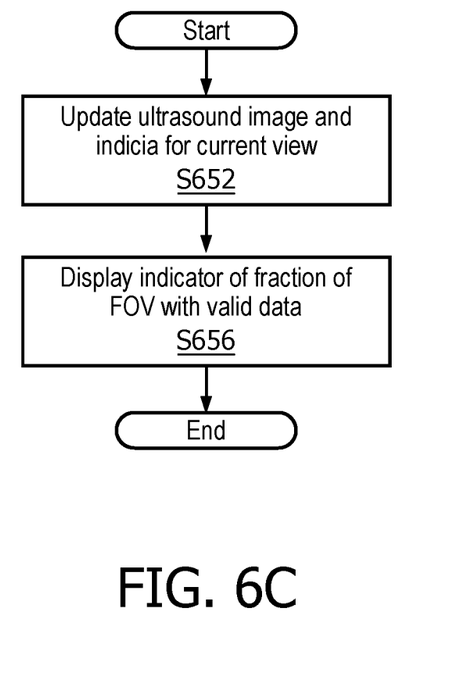
FIG. 6C is a flow chart of an example of updating presentation on a display, in accordance with the present invention.

FIG. 6C is a more detailed description of updating or refreshing the onscreen presentation in step S550. Both the ultrasound image 204 and the indicia 244, 248 are updated for the current onscreen view (step S652). Since the just prior update, movement of the field of view 216, either by movement of the probe or rotation of the imaging plane, may have occurred. Therefore, the frame buffer is updated not only with the currently acquired ultrasound imaging for rendering an ultrasound image, but with graphics such as the indicia 244, 248 as overlays. The current onscreen view may accordingly have one or more fan-shaped images 204 with their respective indicia 244, 248. An ongoing indicator of the fraction of sampled locations within the field of view 216 that have valid data is also displayed onscreen (step S656), after having been refreshed to a current value. More specifically, the coherence count that has been incremented repeatedly in step S620 is divided by the total number of sampled locations $(r, \theta)$ to compute the fraction.

An alternative to the above-described coherence estimation is use of a coherence factor calculated by processing complex-valued channel data. The coherence factor is defined as $$CF(r, \theta) \equiv \frac{\left|\sum_{j=1}^{N} S_j(r, \theta)\right|^2}{N \sum_{j=1}^{N} |S_j(r, \theta)|^2},$$

where r is the depth along beam direction, $\theta$ is the beam direction, $S_j(r, \theta)$ is the complex-valued channel data at depth r received by the j-th channel after applying the focusing delay, and N is the number of channels. The term $$\sum_{j=1}^{N} S_j(r, \theta) \left(\text{or} \left|\sum_{j=1}^{N} S_j(r, \theta)\right|\right)$$

in the numerator represents an image as a function of r and $\theta$ after coherent beamforming but before scan conversion and logarithmic compression. No more than a single beamformer is required. $CF(r, \theta)$ substitutes for the correlation coefficient $\rho(r, \theta)$ in the above-discussed mapping and indicium determination.

In the above-described embodiments, it is assumed that continuous ultrasound acquisition is accompanied with continuous update of the onscreen display. Alternatively, the onscreen display can be updated only when the field of view 216 changes. Thus, the updating can be responsive to probe movement detectable by an integrated electromagnetic (EM) sensor, as well as to image plane movement such as rotation. An example of such an EM sensor is seen in commonly-owned U.S. Pat. No. 7,933,007 to Stanton et al., the entire disclosure of which is incorporated herein by reference.

An interactive visual guidance tool for an imaging acquisition and display system and configured for user navigation with respect to a blockage of a field of view detects, and spatially defines, the blockage. It also integrates, with the image for joint visualization, an indicium that visually represents the definition. The indicium is moved dynamically according to movement, relative to the blockage, of the field of view. The indicium can be shaped like a line segment, or two indicia can be joined in a "V" shape to frame a region of non-blockage. The defining may be based on determining whether ultrasound beams in respective directions are blocked. Included, for deriving the image, in some embodiments are imaging channels for receiving image data for which a metric of coherence, i.e., similarity among channel data, is computed. The determination for a direction is based on the metric for locations in that direction. One application is navigating an ultrasound probe between blocking ribs to achieve a standard cardiac view.

In addition to making diagnostic cardiac examination performable by nurses or other clinicians who may be untrained specifically in sonography, the interactive visual guidance tool 108 can guide novice sonographers. The tool 108 can feature, for this purpose or this mode, a regular (grayscale) sonogram, along with the visual feedback described herein above. Alternatively, the novel visual feedback of the tool 108 can speed up the work flow of trained or experienced sonographers. The ultrasound technician interactive guidance apparatus 100, which includes the tool 108, may encompass a more comprehensive interactive visual guidance system such as that disclosed in commonly-assigned patent application entitled "Anatomically Intelligent Echocardiography for Point-of-Care" to Radulescu et al.

While the invention has been illustrated and described in detail in the drawings and foregoing description, such illustration and description are to be considered illustrative or exemplary and not restrictive; the invention is not limited to the disclosed embodiments.

For example, instead of hash marks on the "V", outwardly pointing arrows may be employed.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. A method for visualizing a blockage region on an ultrasound image, comprising the steps of:
   obtaining from a transducer array of an ultrasound probe ultrasound data representative of an anatomy within a field of view;
   receiving the ultrasound data at a processor via a plurality of data channels in communication with the ultrasound probe;
   applying delays to the received ultrasound data;
   generating an ultrasound image of the field of view including the anatomy within the field of view based on the ultrasound data;
   detecting and spatially defining a blockage region of the ultrasound image comprising a portion of the field of view and associated with an anatomical structure within the anatomy based on the ultrasound data and by computing a metric of similarity for the ultrasound data to which the delays have been applied;
   generating a graphical representation based on the detection and spatial definition of the blockage region;
   integrating the graphical representation with the ultrasound image to form a joint visualization comprising the graphical representation overlaid on the anatomy in the ultrasound image to identify the portion of the field of view corresponding to the blockage region in the ultrasound image;
   automatically outputting the joint visualization, to a display in communication with the processor; and
   moving the joint visualization dynamically in response to a movement of the field of view relative to the blockage.

2. The method of claim 1, wherein the obtaining step further comprises activating a plurality of different apertures, dividing the apertures among the plurality of data channels; and
   beamsumming the ultrasound data obtained from the different apertures,
   wherein the metric of similarity is representative of a correlation between the beamsummed data of the different apertures.

3. The method of claim 2, wherein at least a portion of the apertures are interleaving complementary apertures.

4. The method of claim 1, wherein the detecting and spatially defining a blockage region step further comprises determining whether an ultrasound beam having a beam direction is blocked.

5. The method of claim 4, wherein the detecting and spatially defining a blockage region step further comprises determining whether the ultrasound beam is blocked in the beam direction by computing a metric of coherence of a portion of the ultrasound data associated with the beam direction.

6. The method of claim 1, wherein the moving the joint visualization step further comprises the steps of:
   generating a plurality of ultrasound images of the anatomy during the movement of the field of view, based on the ultrasound data;
   generating a plurality of graphical representations to respectively indicate the blockage region for the plurality of ultrasound images;
   integrating the plurality of graphical representations with the plurality of ultrasound images to form plurality of joint visualizations; and
   outputting the plurality of joint visualizations in response to the movement of the field of view.

7. A method for generating interleaving complementary imaging apertures, comprising the steps of:
   generating with an ultrasound probe a plurality of interleaving complementary imaging apertures;
   forming a correlation map based on data received by channels of the plurality of interleaving complementary imaging apertures of the generating step;
   setting a blockage boundary line using the processor, based on values of the correlation map of the forming step;
   acquiring an ultrasound image in a field of view for display with the blockage boundary line shown as an overlay;
   updating the ultrasound image in response to movement of the field of view;
   determining whether to generate additional interleaving complementary imaging apertures;
   based on the determining step, generating additional interleaving complementary imaging apertures; and
   repeating the generating, forming, setting, and acquiring steps.

8. The method of claim 7, wherein the forming step further comprises delaying and beamsumming imaging data of the data received by the interleaving complementary imaging apertures, and correlating the beamsummed data of one of the interleaving complementary imaging apertures to another of the interleaving complementary imaging apertures.

9. The method of claim 7, wherein the updating step further comprises updating an indicator, correlated to the blocking boundary line, of a fraction of sampled locations within the field of view that have valid imaging data in the ultrasound image.

* * * * *